United States Defensive Publication [19] (H) [11] T100,903

Radel et al. [43] Aug. 4, 1981

[54] PREPARATION OF NITROGEN FERTILIZERS FROM OXALATE ESTERS PREPARED BY THE OXIDATIVE CARBONYLATION OF ALCOHOLS OVER NOBLE METAL CATALYSTS UTILIZING REGENERABLE 2,5-CYCLOHEXADIENE-1,4-DIONE OXIDANTS

[76] Inventors: Robert J. Radel, 1833 W. Tannehill; Jack M. Sullivan, 106 Patsy Dr., both of Florence, Ala. 35630

[21] Appl. No.: 137,204

[22] Filed: Apr. 4, 1980

[51] Int. Cl.[3] ..... C07C 50/04; C07C 67/36; C07C 102/00; C07C 102/06

[52] U.S. Cl. ..... 260/396 R; 560/204; 564/136

[57] ABSTRACT

A process for the preparation of nitrogen fertilizers, especially oxamide, either indirectly or directly from oxalate esters, including the regeneration of the quinone oxidant utilized in the formation of the above esters.

Preparation of oxalate esters by the oxidative carbonylation of alcohols with carbon monoxide in the presence of a catalytic amount of a platinum group metal salt with or without a corresponding metal oxidant salt and an optionally substituted quinone. High yields of isolated dialkyl oxalates are obtained by regulating temperature and carbon monoxide pressure and by maintaining essentially anhydrous conditions. In addition, high yields of the hydroquinones (1,4-dihydroxybenzenes) are recovered.

Preparation of oxamide, a potential slow-release nitrogen fertilizer via the oxidative carbonylation of alcohols with carbon monoxide in the presence of a catalytic amount of a platinum group metal salt and an optionally substituted quinone followed by ammoniation of the filtered reaction mixture at room temperature, or below. High yields of isolated oxamide were obtained by regulating the temperature and pressure during the oxidative carbonylation and maintaining essentially anhydrous conditions throughout the process. In addition, nearly quantitative yields of the hydroquinones (1,4-dihydroxybenzenes) are recovered for recycle along with the solvents.

54 Claims, No Sheets Drawing,

44 Pages Specification

The file of this unexamined application may be inspected and copies thereof may be purchased (849 O.G. 1221, Apr. 9, 1968).